US010709310B2

(12) United States Patent
Aoyama

(10) Patent No.: US 10,709,310 B2
(45) Date of Patent: Jul. 14, 2020

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 173 days.

(21) Appl. No.: 16/004,433

(22) Filed: Jun. 11, 2018

(65) Prior Publication Data

US 2018/0289240 A1 Oct. 11, 2018

Related U.S. Application Data

(63) Continuation of application No. PCT/JP2016/084378, filed on Nov. 21, 2016.

(30) Foreign Application Priority Data

Dec. 22, 2015 (JP) .................................. 2015-250539

(51) Int. Cl.
*A61B 1/00* (2006.01)
*A61B 1/04* (2006.01)
(Continued)

(52) U.S. Cl.
CPC ............ *A61B 1/00009* (2013.01); *A61B 1/00* (2013.01); *A61B 1/00006* (2013.01);
(Continued)

(58) Field of Classification Search
CPC ... A61B 1/00009; A61B 1/00; A61B 1/00006; A61B 1/04; A61B 1/041; A61B 1/06;
(Continued)

(56) References Cited

U.S. PATENT DOCUMENTS

2009/0036741 A1* 2/2009 Igarashi ............... A61B 1/0638
600/160
2013/0006109 A1 1/2013 Takei et al.
(Continued)

FOREIGN PATENT DOCUMENTS

EP 2818096 12/2014
JP 103261295 11/1991
(Continued)

OTHER PUBLICATIONS

"International Search Report (Form PCT/ISA/210) "of PCT/JP2016/084378, dated Feb. 21, 2017, with English translation thereof, pp. 1-3.
(Continued)

*Primary Examiner* — Leon Flores
(74) *Attorney, Agent, or Firm* — JCIPRNET

(57) ABSTRACT

An endoscope system 10 includes an image acquiring unit 54 that acquires a first image and a second image, the first image being obtained by using first illumination light, the second image being obtained by using second illumination light at a different timing from the first image; a halation-region detecting unit 74 that detects a halation region; a calculated-image generating unit 73 that performs calculation by using the first image and the second image and that generates a calculated image; a display-image generating unit 77 that generates a display image in which a tone reflects the calculated image; and a tone changing unit 75 that changes the tone of the halation region in the display image.

18 Claims, 12 Drawing Sheets

(51) Int. Cl.
*H04N 7/18* (2006.01)
*G02B 23/24* (2006.01)
*A61B 1/06* (2006.01)
*A61B 1/07* (2006.01)
*H04N 9/64* (2006.01)

(52) U.S. Cl.
CPC ............ *A61B 1/00045* (2013.01); *A61B 1/04* (2013.01); *A61B 1/041* (2013.01); *A61B 1/06* (2013.01); *A61B 1/0638* (2013.01); *A61B 1/0669* (2013.01); *A61B 1/07* (2013.01); *G02B 23/24* (2013.01); *H04N 7/18* (2013.01); *H04N 9/643* (2013.01)

(58) Field of Classification Search
CPC ....... A61B 1/0638; A61B 1/0669; A61B 1/07; G02B 23/24; H04N 7/18; H04N 9/643
See application file for complete search history.

(56) References Cited

U.S. PATENT DOCUMENTS

2014/0152790 A1 6/2014 Saito et al.
2015/0094538 A1 4/2015 Terakawa

FOREIGN PATENT DOCUMENTS

| | | |
|---|---|---|
| JP | 2000115792 | 4/2000 |
| JP | 2003093338 | 4/2003 |
| JP | 2009118988 | 6/2009 |
| JP | 2015066050 | 4/2015 |
| WO | 2013035531 | 3/2013 |

OTHER PUBLICATIONS

"Written Opinion of the International Searching Authority (Form PCT/ISA/237)" of PCT/JP2016/084378, dated Feb. 21, 2017, with English translation thereof, pp. 1-6.

"Search Report of Europe Counterpart Application", dated Nov. 30, 2018, p. 1-p. 5.

* cited by examiner

ENDOSCOPE SYSTEM, PROCESSOR DEVICE, AND METHOD FOR OPERATING ENDOSCOPE SYSTEM

CROSS-REFERENCE TO RELATED APPLICATIONS

This application is a Continuation of PCT International Application No. PCT/JP2016/084378 filed on Nov. 21, 2016, which claims priority under 35 U.S.C. § 119(a) to Japanese Patent Application No. 2015-250539 filed on Dec. 22, 2015. Each of the above application(s) is hereby expressly incorporated by reference, in its entirety, into the present application.

BACKGROUND OF THE INVENTION

1. Field of the Invention

The present invention relates to an endoscope system that generates an image for display by using two images captured at different timings, a processor device, and a method for operating the endoscope system.

2. Description of the Related Art

In the medical field, with an endoscope system including a light source device, an endoscope, and a processor device, an observation target is typically observed and diagnosed by using an almost real-time motion picture. In addition, the following endoscope system is also known. The endoscope system not only is used for natural observation of the observation target, but also is used to obtain an image in which a tissue of interest, such as a blood vessel, or a structure of interest, such as a duct structure (so-called pit pattern), is emphasized by using light beams in an extremely narrow wavelength band (hereinafter referred to as narrow-band light) such as blue and green as illumination light.

In a case of obtaining an image in which the tissue or structure of interest is emphasized, two images obtained by imaging the observation target at different timings are often used. For example, the following endoscope system is known (JP2015-066050A). In this endoscope system, the observation target is imaged by using different illumination light beams to obtain two images, and one of the two images is combined with a difference image between the two images. Thus, an image representing the depth of a blood vessel by using brightness is generated and displayed. In addition, two images obtained by imaging the observation target at different timings may also be used to extract or emphasize a tissue or structure of interest or to calculate biological function information such as an oxygen saturation.

Besides, in an endoscope system, a blood-vessel emphasizing method for emphasizing a blood vessel by increasing a saturation to increase the visibility of the blood vessel with respect to mucous membranes is known (JP2003-093338A). In a case in which images of a plurality of colors are simultaneously acquired, correction of each pixel having a large pixel value according to color may generate a false color. Thus, an endoscope system that reduces (suppresses) the pixel value while maintaining the color balance is known (JP2000-115792A). An endoscope system that detects and corrects a color shift (false color) is also known (JP1991-261295A (JP-H03-261295A)).

SUMMARY OF THE INVENTION

In a case of generating an image for display (hereinafter referred to as a display image) in which a tissue of interest is emphasized, for example, by using two images, an observation target represented in each image is typically aligned between the two images used, thereby accurately emphasizing, for example, the tissue of interest or the like.

On the other hand, depending on the shape of the observation target and the irradiation direction of the illumination light, the reflectance of the illumination light may locally increase to an extreme degree. This may generate a so-called halation region in which the pixel value is saturated in the captured image. Even a slight movement of the observation target may cause the position of the halation region to move by a comparably large amount. Thus, in the alignment of the observation target, typically, it is not possible to accurately align the position of the halation region. Therefore, when generating a display image by using two images of different colors (that is, illumination light beams are different), halation, if any, in the two images used generates a false color as a result of a color shift in the halation region. The false color in the halation region is particularly obvious if a display image in which a tone reflects a calculation result (e.g., difference) of the images used, and may interfere with the observation of the observation target. Accordingly, it is desirable that a false color be not generated in the halation region.

According to JP2000-115792A, when generating a display image by using three images of different colors, which are simultaneously captured and do not need to be aligned, the images of the respective colors are corrected so as to prevent generation of a false image. However, as described above, it is not possible to prevent generation of a false color when generating a display image by using two images of different colors, which are acquired at different timings. In addition, JP1991-261295A (JP-H03-261295A) discloses that a false color is detected and corrected when generating a display image by using three images of different colors acquired at different timings, which corresponds to the above-described alignment of the observation target. Thus, by the method disclosed in JP1991-261295A (JP-H03-261295A), the misalignment of the halation region remains even after the alignment of the observation target. Therefore, it is not possible to reduce the false color of the halation region.

An object of the present invention is to provide: an endoscope system that reduces a false color in a halation region when generating a display image in which a tone reflects a calculated image obtained by performing calculation by using two images obtained by imaging an observation target by using different illumination light beams at different timings; a processor device; and a method for operating the endoscope system.

An endoscope system according to the present invention includes an image acquiring unit that acquires a first image and a second image, the first image being obtained by imaging an observation target by using first illumination light, the second image being obtained by imaging the observation target by using second illumination light that is different from the first illumination light at a different timing from the first image; a halation-region detecting unit that detects a halation region from at least one of the first image or the second image; a calculated-image generating unit that performs calculation by using the first image and the second image and that generates a calculated image; a display-image generating unit that generates a display image in which a tone reflects the calculated image; and a tone changing unit that changes the tone of the halation region in the display image.

The tone changing unit preferably corrects at least a pixel value of the calculated image to change the tone of the display image.

The tone changing unit preferably changes at least one of a saturation, a hue, or a brightness.

The tone changing unit preferably suppresses the saturation of the halation region in the display image.

The tone changing unit preferably makes the halation region in the display image have an achromatic color.

The tone changing unit preferably suppresses a degree of the pixel value of the calculated image to a threshold.

When generating the display image, the display-image generating unit preferably adds a weight to the calculated image and assigns the obtained calculated image to a chroma channel, and the tone changing unit preferably adjusts the threshold by using the weight of the calculated image.

The display-image generating unit preferably assigns any one of the first image and the second image to a luminance channel and assigns the calculated image to the chroma channel to generate the display image, the halation-region detecting unit preferably detects the halation region from the one of the first image and the second image assigned to the luminance channel, and the tone changing unit preferably changes at least a tone of the halation region in the display image, the halation region being detected from the one of the first image and the second image assigned to the luminance channel.

The tone changing unit preferably changes the tone of the halation region in the first image and the tone of the halation region in the second image.

The calculated-image generating unit preferably generates, as the calculated image, a difference image between the first image and the second image.

The halation-region detecting unit preferably detects the halation region by using a histogram representing an appearance frequency of the pixel value.

The halation-region detecting unit preferably detects the halation region in a specific pixel-value range in a direction from a maximum pixel value to a smaller pixel value.

The halation-region detecting unit preferably detects a peak of a valley of the histogram in the specific pixel-value range and detects, as the halation region, a set of pixels having pixel values larger than or equal to a pixel value at the peak of the valley and smaller than or equal to the maximum pixel value.

The endoscope system preferably further includes a smoothing unit that smooths the calculated image to be used by the display-image generating unit to generate the display image.

A processor device according to the present invention includes an image acquiring unit that acquires a first image and a second image, the first image being obtained by imaging an observation target by using first illumination light, the second image being obtained by imaging the observation target by using second illumination light that is different from the first illumination light at a different timing from the first image; a halation-region detecting unit that detects a halation region from at least one of the first image or the second image; a calculated-image generating unit that performs calculation by using the first image and the second image and that generates a calculated image; a display-image generating unit that generates a display image in which a tone reflects the calculated image; and a tone changing unit that changes the tone of the halation region in the display image.

A method for operating an endoscope system according to the present invention includes a step in which an image acquiring unit acquires a first image and a second image, the first image being obtained by imaging an observation target by using first illumination light, the second image being obtained by imaging the observation target by using second illumination light that is different from the first illumination light at a different timing from the first image; a step in which a halation-region detecting unit detects a halation region from at least one of the first image or the second image; a step in which a calculated-image generating unit performs calculation by using the first image and the second image and that generates a calculated image; a step in which a display-image generating unit generates a display image in which a tone reflects the calculated image; and a step in which a tone changing unit changes the tone of the halation region in the display image.

With the endoscope system, the processor device, and the method for operating the endoscope system according to the present invention, a false color in a halation region can be reduced by changing the tone of the halation region when generating a display image in which the tone reflects a difference between two images by using the two images obtained by imaging an observation target by using different illumination light beams at different timings.

DESCRIPTION OF THE PREFERRED EMBODIMENTS

Figure 1:
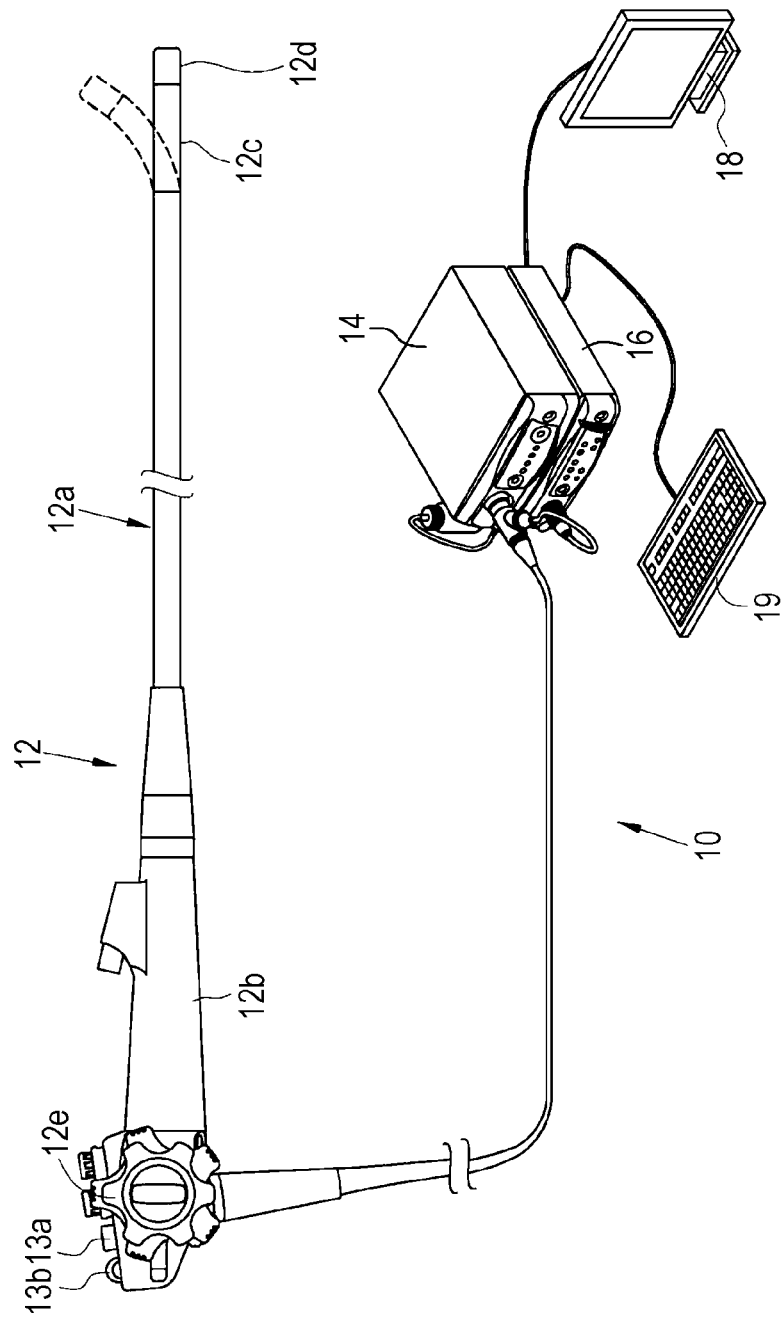
FIG. 1 is an external view of an endoscope system.

As illustrated in FIG. 1, an endoscope system 10 has an endoscope 12, a light source device 14, a processor device 16, a monitor 18, and a console 19. The endoscope 12 is optically connected to the light source device 14 and is electrically connected to the processor device 16. The endoscope 12 has an insertion part 12a to be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result of the bending of the bending part 12c, the tip part 12d is oriented in a desired direction.

In addition, the operating unit 12b is provided with, in addition to the angle knob 12e, a mode switch 13a and a zoom operating unit 13b. The mode switch 13a is used for operation of switching an observation mode. The endoscope system 10 has a normal observation mode and a special observation mode. The normal observation mode is an observation mode for displaying, on the monitor 18, an image with natural colors (hereinafter referred to as a normal image) obtained by imaging an observation target by using white light as illumination light. The special observation mode is an observation mode for displaying, by using images obtained by imaging an observation target, an image in which a blood vessel at a specific depth among blood vessels included in the observation target is emphasized.

The processor device 16 is electrically connected to the monitor 18 and the console 19. The monitor 18 outputs and displays images in the respective observation modes and image information and the like accompanying the images. The console 19 serves as a user interface that receives an input operation for setting functions and the like. Note that an external recording unit (omitted from illustration) that records images, image information, and the like may be connected to the processor device 16.

Figure 2:
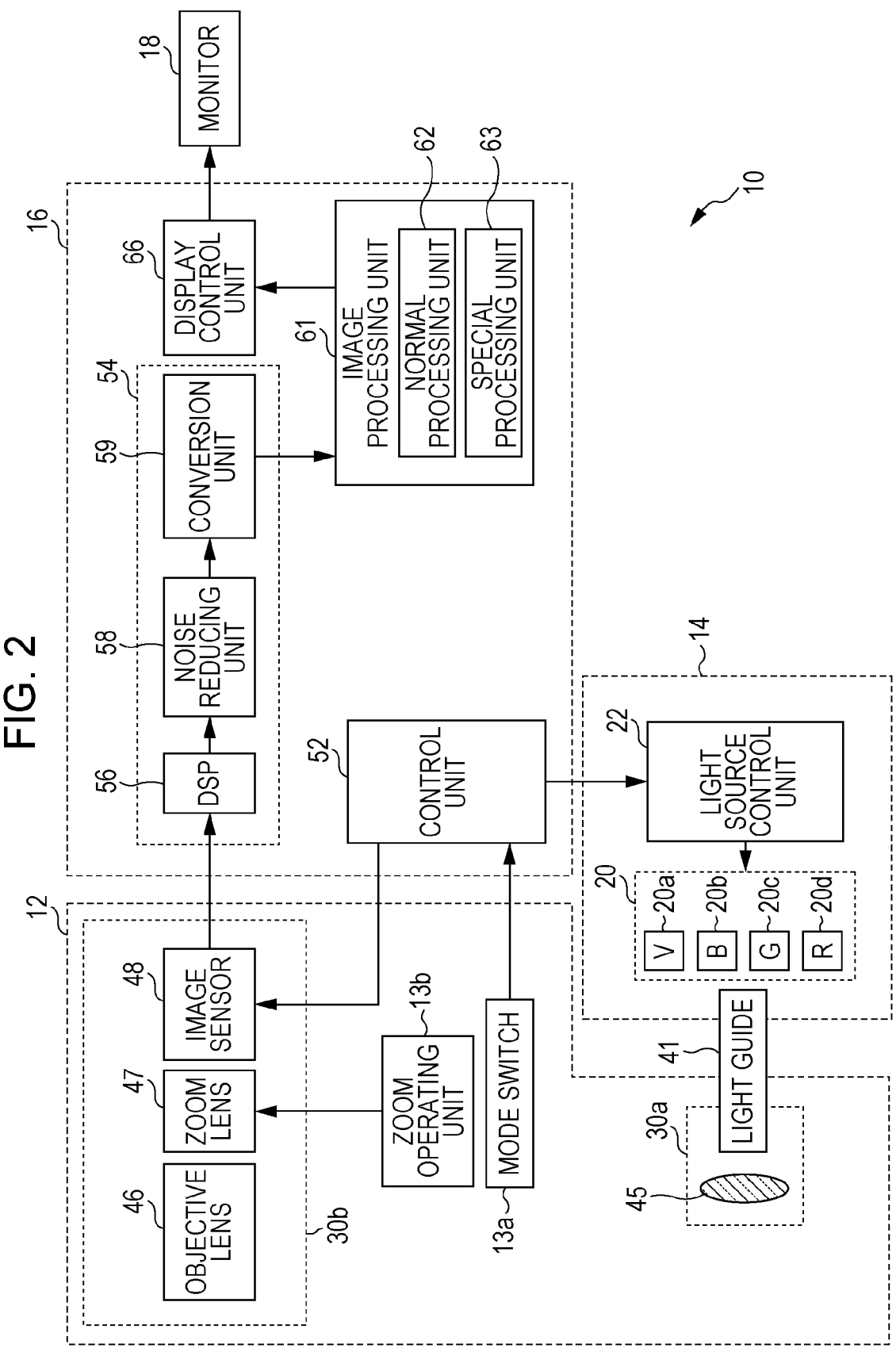
FIG. 2 is a block diagram of the endoscope system.

As illustrated in FIG. 2, the light source device 14 includes a light source unit 20 that emits illumination light and a light source control unit 22 that controls driving of the light source unit 20.

The light source unit 20 includes four light sources, which are a V light source 20a, a B light source 20b, a G light source 20c, and an R light source 20d. In this embodiment, the V light source 20a, the B light source 20b, the G light source 20c, and the R light source 20d are each a light emitting diode (LED). For the light source unit 20, instead of these LEDs, a combination of a laser diode (LD), a fluorescent body, and a band limiting filter, a combination of a lamp such as a xenon lamp and a band limiting filter, and the like can be used.

The V light source 20a is a violet light source that emits violet light V with a center wavelength of about 405 nm and a wavelength band of about 380 nm to 420 nm. The B light source 20b is a blue light source that emits blue light B with a center wavelength of about 460 nm and a wavelength band of about 420 nm to 500 nm. The G light source 20c is a green light source that emits green light G with a wavelength band of about 480 nm to 600 nm. The R light source 20d is a red light source that emits red light R with a center wavelength of about 620 nm to 630 nm and a wavelength band of about 600 nm to 650 nm. Note that the center wavelengths of the V light source 20a and the B light source 20b have a margin of about ±5 nm to ±10 nm.

The light source control unit 22 independently controls timings for turning on and off the respective light sources 20a to 20d constituting the light source unit 20, light emission amounts at the time of turning on, and the like. In the normal observation mode, the light source control unit 22 turns on all of the V light source 20a, the B light source 20b, the G light source 20c, and the R light source 20d. Thus, in the normal observation mode, the illumination light is white light including the violet light V, the blue light B, the green light G, and the red light R.

On the other hand, in the special observation mode, first illumination light and second illumination light different from the first illumination light are selected by setting and used. Thus, in the special observation mode, the light source control unit 22 controls the light sources 20a to 20d of the respective colors between an emission pattern in which the first illumination light is emitted and an emission pattern in which the second illumination light is emitted.

For example, if the first illumination light and the second illumination light selected by setting is the violet light V and the blue light B, the light source control unit 22 alternately repeats an emission pattern in which only the V light source 20a is turned on and an emission pattern in which only the B light source 20b is turned on. In addition, if the first illumination light and the second illumination light selected by setting is the blue light B and the green light G, the light source control unit 22 alternately repeats an emission pattern in which only the B light source 20b is turned on and an emission pattern in which only the G light source 20c is turned on.

Of course, the red light R can be used as the first illumination light or the second illumination light. In addition, single-color light emitted by using any one of the light sources 20a to 20d of the respective colors can be used as the first illumination light or the second illumination light, and furthermore, light emitted by turning on two or more light sources among the light sources 20a to 20d of the respective colors can also be used as the first illumination light or the second illumination light. In a case in which the first illumination light or the second illumination light is emitted by turning on a plurality of light sources, by changing the whole spectrum by adjusting the balance of light amounts of light sources to be turned on, light having various colors can be used as the first illumination light or the second illumination light even if the combination of the light sources to be turned on is the same. Of light having each color emitted from any of the light sources 20a to 20d of the respective colors, light in which a part of the wavelength band or the light amount is limited by using a band limiting filter can also be used as the first illumination light or the second illumination light. Therefore, "different" illumination light herein means at least one of the wavelength band or the spectrum is not the same when two illumination light beams are compared with each other.

Illumination light emitted from the light source unit 20 enters a light guide 41. The light guide 41 is incorporated in the endoscope 12 and a universal cord (cord connecting the endoscope 12, the light source device 14, and the processor device 16), and the illumination light propagates therethrough to the tip part 12d of the endoscope 12. Note that a multi-mode fiber can be used as the light guide 41. As an example, a small-diameter fiber cable having a core diameter of 105 µm, a clad diameter of 125 µm, and a diameter of Ø0.3 to 0.5 mm including a protective layer serving as an outer skin can be used.

The tip part 12d of the endoscope 12 is provided with an illumination optical system 30a and an imaging optical system 30b. The illumination optical system 30a has an illumination lens 45, and an observation target is irradiated with illumination light through the illumination lens 45. The imaging optical system 30b has an objective lens 46, a zoom lens 47, and an image sensor 48. The image sensor 48 images the observation target by using, for example, reflected light or scattered light (including fluorescence emitted from the observation target or fluorescence caused by medicine that is, for example, given to the observation target) of illumination light returning from the observation target through the objective lens 46 and the zoom lens 47. Note that the zoom lens 47 is moved by operating the zoom operating unit 13b and zooms in or zooms out the observation target imaged by the image sensor 48.

The image sensor 48 is a color sensor of the primary color system and has three types of pixels: a B pixel (blue pixel) provided with a blue color filter that mainly transmits light of a violet to blue wavelength band; a G pixel (green pixel) provided with a green color filter that mainly transmits light of a green wavelength band; and an R pixel (red pixel) provided with a red color filter that mainly transmits light of a red wavelength band. Accordingly, when the observation target is imaged by the image sensor 48, three types of images, which are a B image (blue image), a G image (green image), and an R image (red image), are obtained.

In the normal observation mode, since the illumination light is white light, as described above, each of the B image, the G image, and the R image is obtained. Specifically, the B pixel images the observation target by receiving light of the violet to blue wavelength band from reflected light or the like of the white light and outputs the B image. The G pixel receives light of the green wavelength band and outputs the G image, and the R pixel receives light of the red wavelength band and outputs the R image.

On the other hand, in the special observation mode, the illumination light is alternately switched between the first illumination light and the second illumination light. Accordingly, an image of the BGR colors obtained by imaging the observation target by using the first illumination light (hereinafter this image will be referred to as a first image) and an image of the BGR colors obtained by imaging the observation target by using the second illumination light at a different timing from the first image (hereinafter this image will be referred to as a second image) are obtained. For example, in a case in which the violet light V is used as the first illumination light and the blue light B is used as the second illumination light, substantially, a B image corresponding to reflected light or the like of the violet light V (hereinafter this image will be referred to as a V image) is the first image, and a B image corresponding to the blue light B is the second image.

Note that a charge coupled device (CCD) sensor or a complementary metal oxide semiconductor (CMOS) sensor can be used as the image sensor 48. In addition, although the image sensor 48 according to this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially imaging the observation target by using illumination light of the respective colors such as BGR, images of the above respective colors can be obtained.

The processor device 16 has a control unit 52, an image acquiring unit 54, an image processing unit 61, and a display control unit 66.

In response to an input of a mode switching signal from the mode switch 13a, the control unit 52 inputs a control signal to the light source control unit 22 and the image sensor 48 to switch the observation mode. In addition, the control unit 52 controls synchronization of an illumination-light irradiation timing and an imaging timing, for example.

The image acquiring unit 54 acquires images of the respective colors from the image sensor 48. Specifically, in the normal observation mode, the image acquiring unit 54 acquires the B image, the G image, and the R image from the image sensor 48. On the other hand, in the special observation mode, the image acquiring unit 54 acquires, from the image sensor 48, the first image obtained by imaging the observation target by using the first illumination light and the second image obtained by imaging the observation target by using the second illumination light different from the first illumination light at a different timing from the first image. For example, in a case in which the first illumination light is the violet light V and the second illumination light is the blue light B, the image acquiring unit 54 sequentially acquires the V image and the B image.

In addition, the image acquiring unit 54 has a digital signal processor (DSP) 56, a noise reducing unit 58, and a conversion unit 59, and performs various kinds of processing on the acquired images by using these units.

The DSP 56 performs various kinds of processing on the acquired images, such as defect correction processing, offset processing, gain correction processing, linear matrix processing, gamma conversion processing, demosaicing processing, and YC conversion processing, as needed.

The defect correction processing is for correcting the pixel value of a pixel corresponding to a defective pixel of the image sensor 48. The offset processing is for setting an accurate zero level by reducing a dark current component from an image subjected to the defect correction processing. The gain correction processing is for adjusting the signal level of each image by multiplying the image subjected to the offset processing by a gain. The linear matrix processing increases the color reproducibility of an image subjected to the offset processing, and the gamma conversion processing is for adjusting the brightness and saturation of an image subjected to the linear matrix processing. The demosaicing processing (also referred to as isotropic processing or synchronization processing) is for interpolating the pixel value of a lacking pixel and is performed on an image subjected to the gamma conversion processing. The lacking pixel is a pixel without a pixel value as a result of arrangement of a pixel of another color in the image sensor 48 for the array of the color filters. For example, since the B image is obtained by imaging the observation target by using the B pixel, there are no pixel values of pixels at positions corresponding to the G pixel and the R pixel in the image sensor 48. The demosaicing processing interpolates the B image and generates the pixel values of the pixels at positions corresponding to the G pixel and the R pixel in the image sensor 48. The YC conversion processing converts an image subjected to the demosaicing processing into a luminance channel Y, a chroma channel Cb, and a chroma channel Cr.

The noise reducing unit 58 performs noise reducing processing on the luminance channel Y, the chroma channel Cb, and the chroma channel Cr, by using, for example, a moving average method or a median filter method. The conversion unit 59 re-converts the luminance channel Y, the chroma channel Cb, and the chroma channel Cr, which have been subjected to the noise reducing processing, into images of BGR colors again.

The image processing unit 61 has a normal processing unit 62 and a special processing unit 63. The normal processing unit 62 operates in the normal observation mode and performs color converting processing, color emphasizing processing, and structure emphasizing processing on the images of BGR colors to generate a normal image. In the color converting processing, the images of BGR colors are subjected to 3×3 matrix processing, gradation transformation processing, three-dimensional look-up table (LUT) processing, and the like. The color emphasizing processing is for emphasizing the colors in an image, and the structure emphasizing processing is, for example, for emphasizing a tissue or a structure of the observation target, such as a blood vessel or a pit pattern. The display control unit 66 sequentially acquires the normal image from the normal processing unit 62 and converts the acquired normal image into an image in a format suitable for display, and sequentially outputs and displays the converted image on the monitor 18. Thus, in the normal observation mode, a physician or the like can observe the observation target by using a motion picture of the normal image.

Figure 3:
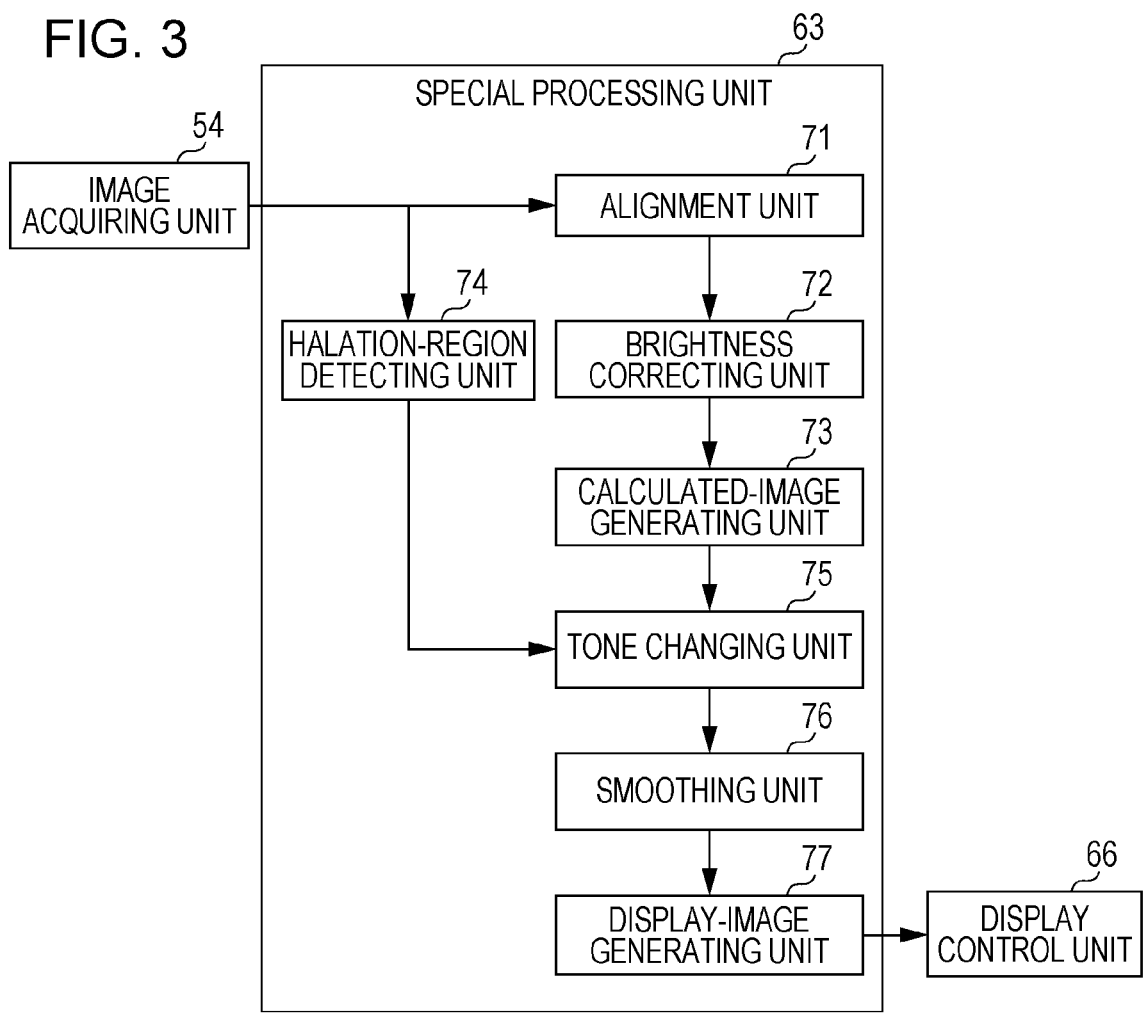
FIG. 3 is a block diagram of a special processing unit.

The special processing unit 63 operates in the special observation mode, and generates, by using the images acquired in the special observation mode, an image representing a blood vessel at a specific depth (e.g., specific depth based on the mucosal surface of the observation target) by using a color that is different from the colors representing the other blood vessels. As illustrated in FIG. 3, the special processing unit 63 includes an alignment unit 71, a brightness correcting unit 72, a calculated-image generating unit 73, a halation-region detecting unit 74, a tone changing unit 75, a smoothing unit 76, and a display-image generating unit 77.

The alignment unit 71 aligns the first image and the second image. The alignment of the first image and the second image (hereinafter simply referred to as alignment) is a process to make the positions (coordinates) of corresponding portions of the observation target represented in the first image and the observation target represented in the second image substantially correspond to each other. For example, the alignment can be performed by estimating a motion vector of the observation target represented in both images by performing matching between the first image and the second image, and by deforming, on the basis of the estimated motion vector, at least one of the first image or the second image.

The brightness correcting unit 72 corrects the brightness of at least one of the first image or the second image aligned by the alignment unit 71, and sets a specific brightness ratio between the first image and the second image. For example, the brightness correcting unit 72 performs gain correction on at least one of the first image or the second image by using a light-amount ratio between the first illumination light and the second illumination light to correct the relative brightness of the first image and the second image.

Since the light amount of the first illumination light at the time of obtaining the first image and the light amount of the second illumination light at the time of obtaining the second image are known when the first image and the second image are obtained, the light-amount ratio between the first illumination light and the second illumination light is known at the stage in which the brightness correcting unit 72 corrects the brightness. Accordingly, for example, if the first illumination light and the second illumination light are the violet light V and the blue light B, respectively, with a light-amount ratio therebetween being 2:1, the brightness correcting unit 72 halves the brightness of the V image (first image) by gain correction, or doubles the brightness of the B image (second image) by gain correction, so as to set the brightness ratio between the V image (first image) and the B image (second image) to 1:1 (specific ratio).

In addition, the average luminance of the first image substantially corresponds to the brightness of the mucous membrane of the observation target represented in the first image. Similarly, the average luminance of the second image substantially corresponds to the brightness of the mucous membrane of the observation target represented in the second image. Accordingly, as described above, instead of using the ratio between the first illumination light and the second illumination light, the brightness correcting unit 72 can also calculate the average luminances of the first image and the second image, and can perform, by using a ratio of the average luminances, gain correction on at least one of the first image or the second image to correct the relative brightness between the first image and the second image to a specific ratio.

The calculated-image generating unit 73 performs calculation by using the first image and the second image with corrected brightness to generate a calculated image. In this embodiment, the calculated-image generating unit 73 calculates a difference between the first image and the second image and generates a difference image A as the calculated image. More specifically, the calculated-image generating unit 73 performs logarithmic transformation on the first image and the second image to generate the difference image A representing the difference between the first image and the second image that are subjected to the logarithmic transformation (more specifically, the difference image A is obtained by subtracting the first image from the second image). The pixel value of each pixel in the first image and the second image represents a light receiving amount, but after the logarithmic transformation, the pixel value represents the concentration. Accordingly, a stable calculation result can be obtained irrespective of the illuminance of the illumination light at the time of obtaining each image. Note that, γ transformation may be performed without limitation to the logarithmic transformation.

Figure 4:
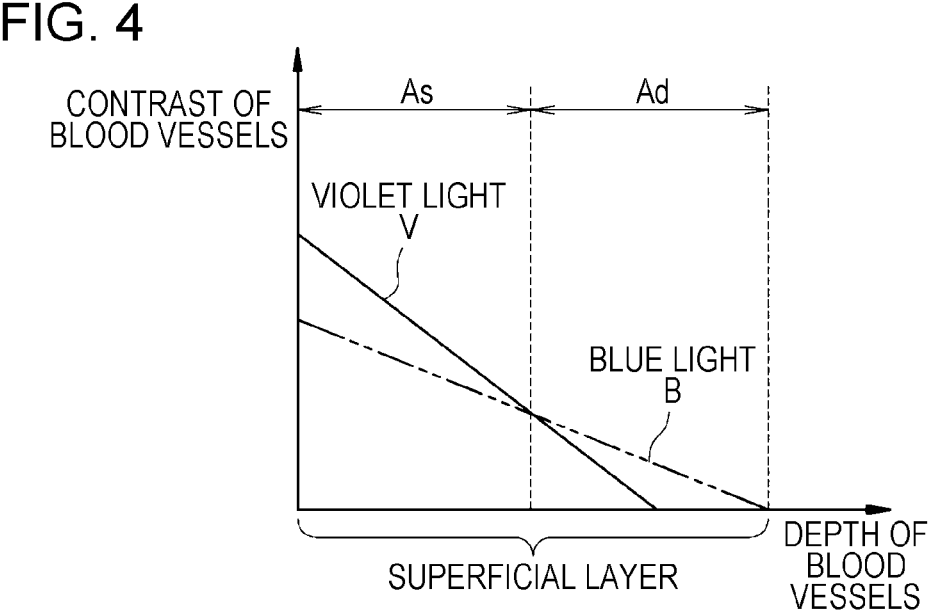
FIG. 4 is a graph schematically illustrating a relationship between the depth of blood vessels and the contrast of the blood vessels.

As described above, generation of the difference image A as the calculated image by the calculated-image generating unit 73 corresponds to emphasizing a blood vessel at a specific depth by using the first image and the second image. For example, as illustrated in FIG. 4, if the violet light V and the blue light B are used as the first illumination light and the second illumination light, so-called superficial blood vessels (blood vessels in all depth ranges As and Ad) in a comparably shallow depth range under the mucous membrane are observable with either illumination light. However, the violet light V has a smaller degree of light reach due to a shorter wavelength than that of the blue light B. Accordingly, in a case in which the violet light V is used as the illumination light, blood vessels in the particularly shallow depth range As (hereinafter referred to as most superficial blood vessels) among the superficial blood vessels are displayed clearly compared with a case in which the blue light B is used as the illumination light. However, blood vessels in the comparably deep depth range Ad among the superficial blood vessels are not displayed clearly. Instead, the contrast of the most superficial blood vessels in the depth range As (ratio of a reflected light amount from the blood vessels to a reflected light amount from a peripheral mucous membrane) is larger than that when using the blue light B as the illumination light. In contrast, the blue light B has a larger degree of light reach as the wavelength is longer than that of the violet light V. Accordingly, if the blue light B is used as the illumination light, blood vessels in the relatively deep depth range Ad can also be displayed clearly compared with a case in which the violet light V is used as the illumination light. Instead, the contrast of the most superficial blood vessels in the particularly shallow depth range As is smaller than that when using the violet light V.

Accordingly, if the difference image A is generated by subtracting, from the V image obtained by using the violet light V as the illumination light, the B image obtained by using the blue light B as the illumination light, in this difference image Δ, the pixel value of each pixel representing a most superficial blood vessel in the depth range As, which is a particularly shallow range under the mucous membrane, among the superficial blood vessels, has a small value (black), and the pixel value of each pixel representing a blood vessel in the depth range Ad, which is deep, among the superficial blood vessels, has a large value (white). Accordingly, if the tissue of interest is a most superficial blood vessel, by using the violet light V as the first illumination light and the blue light B as the second illumination light, in the difference image A generated by subtracting the B image from the V image, the most superficial blood vessel in the specific depth range As is emphasized by using the contrast.

Note that, on the contrary to the above method, if the difference image A is generated by subtracting the V image from the B image, in the difference image Δ, the pixel value of each pixel representing the most superficial blood vessel in the depth range As has a large value (white), and the pixel value of each pixel representing a blood vessel in the depth range Ad has a small value (black). Accordingly, even in a case in which the combination of the violet light V and the blue light B is used as the first illumination light and the second illumination light as in the above case, by using the blue light B as the first illumination light and the violet light V as the second illumination light, in the difference image Δ generated by subtracting the B image from the V image, the blood vessel in the specific depth range Ad is emphasized by using contrast.

The halation-region detecting unit 74, for example, acquires the first image or the second image from the image acquiring unit 54 and detects a halation region from at least one of the first image or the second image. In this embodiment, the halation-region detecting unit 74 detects the halation region from only one of the first image and the second image. In addition, the halation-region detecting unit 74 does not freely select an image from the first image and the second image for detecting halation, but detects the halation from an image, from the first image and the second image, used by the display-image generating unit 77 to generate a display image. Specifically, the display-image generating unit 77 assigns either the first image or the second image to the luminance channel of the display image to be used, and thus, the halation-region detecting unit 74 detects the halation from either the first image or the second image assigned to the luminance channel by the display-image generating unit 77.

Figure 5:
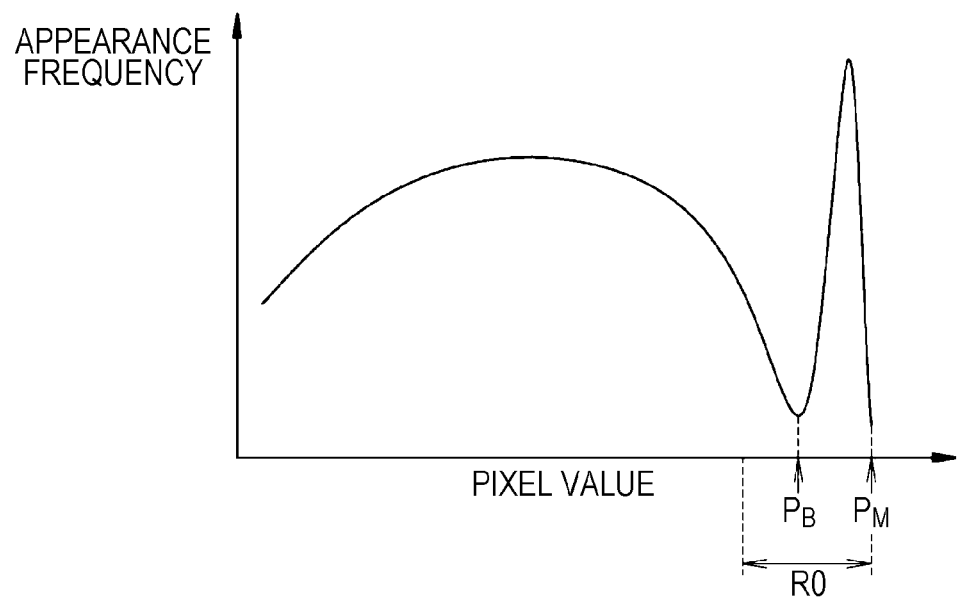
FIG. 5 is a histogram used for detecting a halation region.

In addition, the detection of the halation region uses a histogram representing the appearance frequency of a pixel value as illustrated in FIG. 5. The halation-region detecting unit 74 starts detecting the halation region form a maximum pixel value $P_M$. This is because the pixel value is saturated or almost saturated in the halation region. In addition, because of the characteristics of the halation region, the detection of the halation region does not have to be performed in the entire range of the histogram. Accordingly, the halation-region detecting unit 74 detects the halation region in a specific pixel-value range R0 in the direction from the maximum pixel value $P_M$ toward a smaller pixel value. In the specific range R0 from the maximum pixel value $P_M$ as described above, the halation-region detecting unit 74 detects a pixel value $P_B$ at the peak of the valley (i.e., bottom) of the histogram. Thus, the halation-region detecting unit 74 detects a set of pixels having the pixel values from the pixel value $P_B$ at the peak of the valley to the maximum pixel value $P_M$ as a halation region. Note that the specific range R0 is a range in which the pixel values are relatively large and are not too large or too small to detect a halation region, the pixel values being necessary and sufficient to detect the halation region on an empirical basis.

In addition, the halation-region detecting unit 74 preferably smooths the edge of the halation region that has been detected in the above manner. This enables the detection of the halation region including its peripheral pixels that might have abnormal pixel values in relation to the halation region. This smoothing can be performed in substantially the same manner as the operation of the smoothing unit 76. A smoothing unit that smooths the edge of the halation region may be provided in addition to the halation-region detecting unit 74. In this case, the smoothing unit 76 can be used for smoothing the edge of the halation region.

The tone changing unit 75 changes the tone of the halation region in the display image generated by the display-image generating unit 77. The tone changed by the tone changing unit 75 means the saturation, hue, or lightness of the display image. The tone changing unit 75 changes at least one of the saturation, hue, or lightness of the display image. In this embodiment, since the display-image generating unit 77 generates a display image in which the tone reflects the difference image Δ, which is a calculated image, the tone changing unit 75 corrects at least the pixel values of the halation region in the difference image Δ. Thus, as a result, the tone changing unit 75 changes the tone of the display image.

In addition, in this embodiment, the tone changing unit 75 suppresses the saturation of the halation region in the display image. Specifically, the display-image generating unit 77 generates the display image by assigning the difference image Δ to the chroma channel, and thus, the tone changing unit 75 suppresses the pixel values of the halation region in the difference image Δ. As a result, the tone changing unit 75 can make the halation region in the display image generated by the display-image generating unit 77 have an achromatic color.

The above-described saturation suppressing process performed by the tone changing unit 75 includes two saturation suppressing processes: a first saturation suppressing process and a second saturation suppressing process. The first saturation suppressing process is a process in which local pixel values of the difference image Δ, which are the pixel values of the halation region detected by the halation-region detecting unit 74, are replaced with approximately zero. The second saturation suppressing process is a general clipping process in which pixel values larger than or equal to a threshold Th are set to ±Th in the entire difference image Δ.

Figure 6:
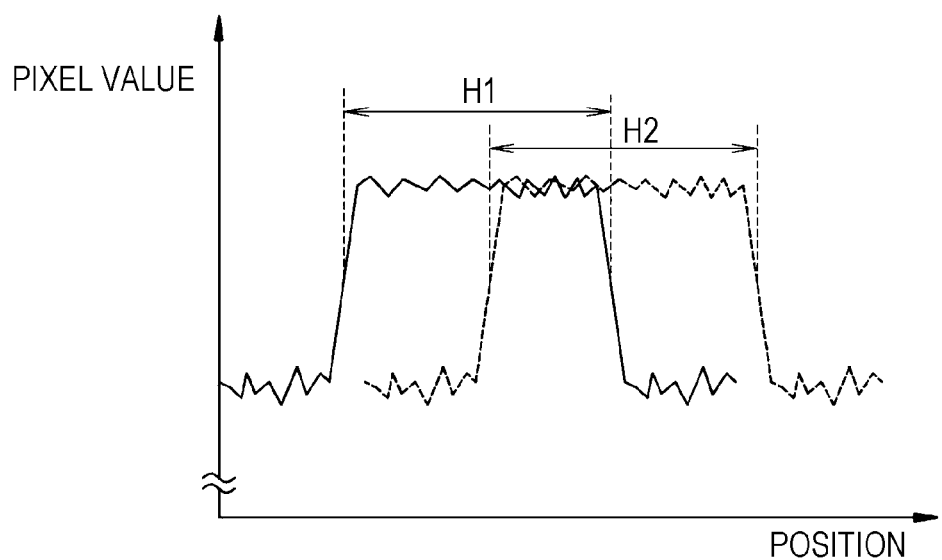
FIG. 6 is a graph illustrating the pixel value of the halation region.
Figure 7:
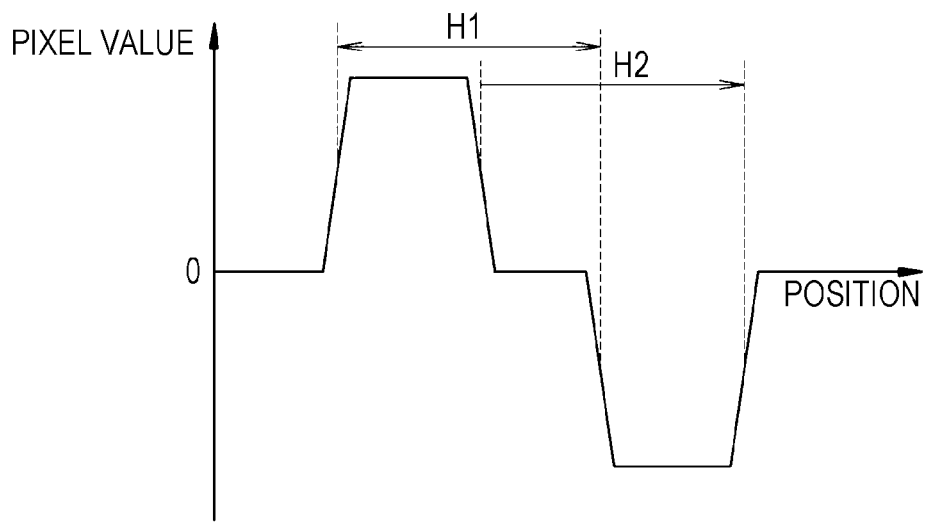
FIG. 7 is a graph illustrating the pixel value of the halation region in a difference image.

For example, as illustrated in FIG. 6, it is assumed that there is a halation region H1 in a certain portion of the first image. In addition, it is assumed that a halation region H2 in the second image is misaligned with the halation region H1 in the first region because the second image is captured at a different timing from the first image. In this case, as illustrated in FIG. 7, in the difference image Δ, a portion of the halation region H1 in the first image, the portion not overlapping with the halation region H2 in the second image, has large pixel values. Similarly, in the difference image Δ, a portion of the halation region H2 in the second image, the portion not overlapping with the halation region H1 in the first image, has small pixel values. In addition, in the difference image Δ, the portion where the halation region H1 in the first image overlaps with the halation region H2 in the second image has approximately zero pixel values.

Figure 8:
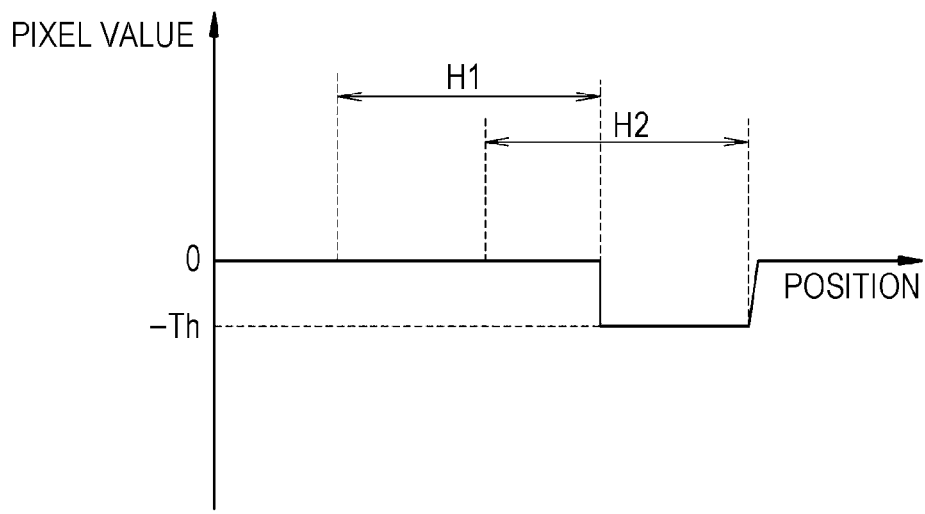
FIG. 8 is a graph illustrating the pixel value of the difference image subjected to a saturation suppressing process.

Accordingly, as illustrated in FIG. 8, by performing the first saturation suppressing process on the difference image Δ, the tone changing unit 75 makes the pixel values of the portion of the halation region H1 in the first image not overlapping with the halation region H2 in the second image approximately zero. As a result, in the display image, the saturation of the halation region H1 in the first image is suppressed. Furthermore, by performing the second saturation suppressing process on the difference image Δ, the tone changing unit 75 clips all the pixel values exceeding ±Th to ±Th. Thus, although the halation-region detecting unit 74 only detects the halation region H1 in the first image and does not detect the halation region H2 in the second image, the tone changing unit 75 reduces the pixel values of the halation region H2 in the second region. In this manner, the tone changing unit 75 performs the second saturation suppressing process so as to suppress the saturation of the halation region H2 in the second image in the display image.

The smoothing unit 76 is a so-called low-pass filter (hereinafter referred to as an LPF) and smooths the calculated image to be used by the display-image generating unit 77 to generate a display image. In this embodiment, the calculated-image generating unit 73 generates the difference image Δ as the calculated image and uses the difference image Δ corrected by the tone changing unit 75 to generate the display image. Accordingly, the smoothing unit 76 smooths the corrected difference image Δ corrected by the tone changing unit 75. Thus, at least the halation region H1 detected by the halation-region detecting unit 74 is smoothed. The processing intensity of smoothing performed by the smoothing unit 76 on the difference image Δ is determined by the cutoff frequency of the LPF. The cutoff frequency of the LPF is set in advance, and the difference image Δ is smoothed to have at least higher smoothness than the original difference image Δ. In addition, the smoothing unit 76 can smooth the difference image Δ by combining enlarging processing and reducing processing. For example, the smoothing unit 76 can perform reducing processing and then can perform enlarging processing.

The display-image generating unit 77 generates a display image in which the tone reflects the calculated image. Specifically, by using either one of the first image and the second image and the calculated image that has been smoothed, the display-image generating unit 77 generates a display image having the luminance channel Y and the two chroma channels Cb and Cr. In this embodiment, the display-image generating unit 77 assigns either of the first image and the second image having a higher contrast of the tissue of interest or the like to the luminance channel Y. In addition, since the calculated-image generating unit 73 generates the difference image Δ as the calculated image, the display-image generating unit 77 assigns the difference image Δ that has been smoothed to the two chroma channels Cb and Cr. Thus, the display-image generating unit 77 generates a display image in which a tissue of interest or the like is emphasized by using the tone.

Figure 9:
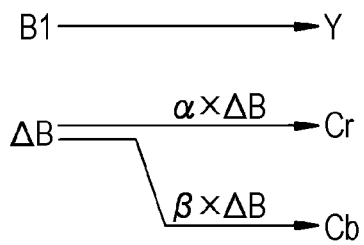
FIG. 9 is an explanatory diagram illustrating a method for generating a display image.

For example, in a case in which the tissue of interest is a most superficial blood vessel, and the violet light V and the blue light B are respectively used as the first illumination light and the second illumination light, as a result of comparison between the V image (first image) and the B image (second image), the contrast of the most superficial blood vessel has a relatively higher contrast in the V image. Accordingly, as illustrated in FIG. 9, the display-image generating unit 77 assigns the V image having a relatively higher contrast of the most superficial blood vessel to the luminance channel Y. In addition, when assigning the difference image Δ to the chroma channels Cb and Cr, multiplication by a factor α (e.g., α=0.169) and a factor β (e.g., R=0.5) is performed to add weights, thereby setting the same color as the color of images displayed by another endoscope system that emphasizes and observes a superficial blood vessel or the like. The thus generated display image has substantially the same color as a whole as images in which a blood vessel or the like is emphasized by a conventional endoscope system, and the most superficial blood vessel is emphasized by using a color different from the colors representing other blood vessels in the mucous membrane, the depth range Ad, and the like. Note that the factor α and the factor β differ depending on the tissue of interest or the like, that is, the combination of the illumination light beams used. Accordingly, the tone changing unit 75 adjusts the value of the threshold Th to be used for the second saturation suppressing process by using the factor β of the difference image Δ.

In a case of the special observation mode, the display control unit 66 sequentially acquires the above display image from the display-image generating unit 77 and sequentially converts the display image into an image in a format suitable for display on the monitor 18 and outputs the image. Thus, in the case of the special observation mode, a physician or the like can observe the observation target by using a motion picture.

Figure 10:
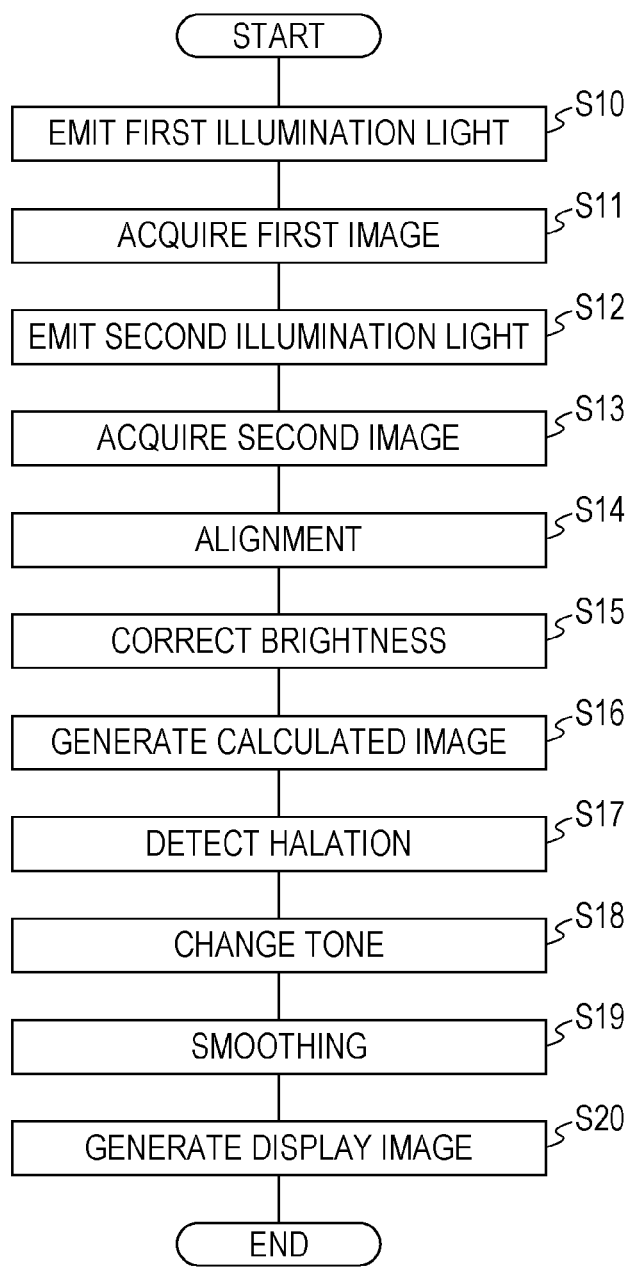
FIG. 10 is a flowchart illustrating an operation flow in a special observation mode.

Next, a flow of image processing performed by the endoscope system 10 in the special observation mode will be described with reference to FIG. 10. Upon the endoscope system 10 being switched to the special observation mode, the light source unit 20 emits first illumination light in accordance with the setting (S10). Subsequently, the image sensor 48 images an observation target irradiated with the first illumination light, and the image acquiring unit 54 acquires a first image corresponding to the first illumination light (S11). Subsequently, the light source control unit 22 switches the illumination light, and the light source unit 20 emits second illumination light (S12). Subsequently, the image sensor 48 images the observation target irradiated with the second illumination light, and the image acquiring unit 54 acquires a second image corresponding to the second illumination light (S13). Subsequently, the alignment unit 71 aligns the first image and the second image (S14), and the brightness correcting unit 72 corrects the brightness of the first image and the second image (S15).

In this embodiment, the following is assumed. The tissue of interest or the like is a most superficial blood vessel, the first illumination light is set as the violet light V, and the second illumination light is set as the blue light B. In this case, the first image is a V image 110, and the second image is a B image 120.

Figure 11:
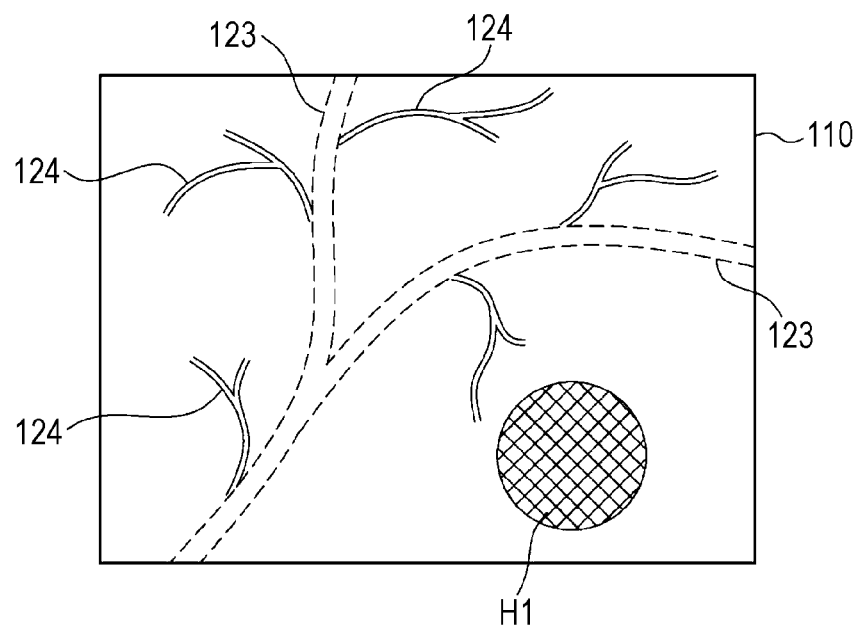
FIG. 11 is a schematic diagram of a V image.

As illustrated in FIG. 11, in the V image 110, which is the first image, a most superficial blood vessel 124 is observable. In addition, a superficial blood vessel 123 at a deeper position than the most superficial blood vessel 124 under the mucous membrane is also observable by using the V image 110. Furthermore, it is assumed that a halation region H1 is in the V image 110.

Figure 12:
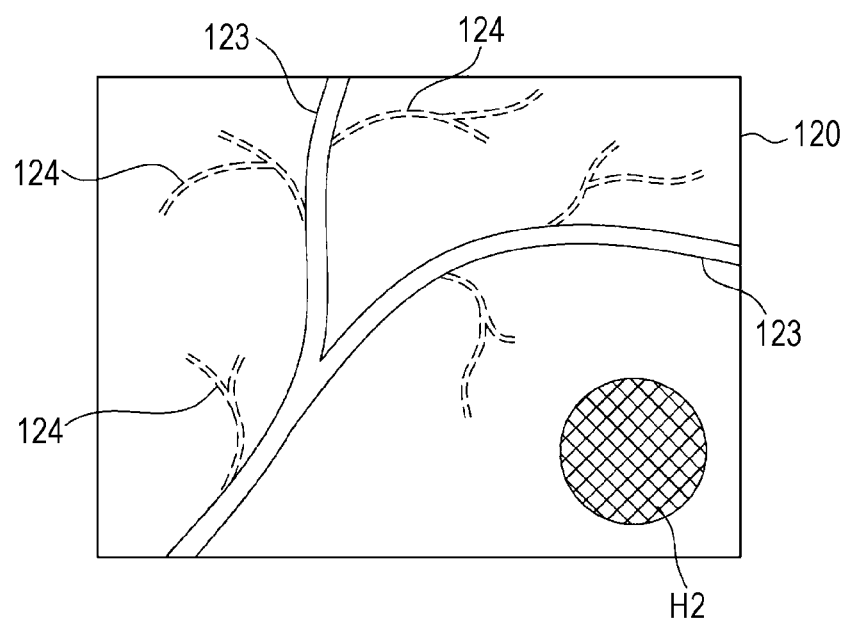
FIG. 12 is a schematic diagram of a B image.

On the other hand, as illustrated in FIG. 12, in the B image 120, which is the second image, the superficial blood vessel 123 at a comparably deep position is observable. In addition, the most superficial blood vessel 124 is also observable by using the B image 120. However, when the V image 110 and the B image 120 are compared with each other, the V image 110 has a higher contrast of the most superficial blood vessel 124, and the B image 120 has a higher contrast of the superficial blood vessel 123 at a deeper position than the most superficial blood vessel 124. In addition, although a halation region H2 is in the B image 120, it is assumed that the halation region H2 in the B image 120 is misaligned with the halation region H1 in the V image 110 even after the alignment of the V image 110 and the B image 120.

Upon the first image and the second image being acquired and the alignment therebetween and brightness correction being completed, the calculated-image generating unit 73 performs calculation by using the first image and the second image to generate a calculated image (S16). In this embodiment, the calculated-image generating unit 73 subtracts the second image from the first image to generate a difference image Δ. Since the structure of interest, the first image, and the second image are respectively the most superficial blood vessel 124, the V image 110, and the B image 120, the calculated-image generating unit 73 subtracts the B image 120 from the V image 110 to generate the difference image Δ illustrated in FIG. 13. In the difference image Δ, compared with the original V image 110 and the B image 120, the superficial blood vessel 123 at a comparatively deep position under the mucous membrane has a large pixel value, and the most superficial blood vessel 124 has a small pixel value. Thus, the difference between the most superficial blood vessel 124 and the superficial blood vessel 123 at a comparatively deep position under the mucous membrane is more obvious than in the V image 110.

The halation regions H1 and H2 also have this feature. That is, since the calculated-image generating unit 73 subtracts the B image 120 from the V image 110, a region A1 of the halation region H1 (hereinafter simply referred to as a region A1), the region not overlapping with the halation region H2, has larger pixel values than the most superficial blood vessel 124. In addition, a region A2 of the halation region H2 (hereinafter simply referred to as a region A2), the region not overlapping with the halation region H1, has smaller pixel values than the superficial blood vessel 123. A region IS in which the halation region H1 overlaps with the halation region H2 (hereinafter referred to as an overlap region IS) has approximately zero pixel values as in the mucous membrane or the like of the observation target.

As described above, while the calculated-image generating unit 73 generates the difference image Δ, the halation-region detecting unit 74 acquires the first image or the second image from the image acquiring unit 54 to detect the halation region (S17). In this embodiment, the tissue of interest or the like is the most superficial blood vessel 124, and the display-image generating unit 77 assigns the V image 110, which is the first image, to the luminance channel Y. Accordingly, the halation-region detecting unit 74 detects the halation region H1 from the V image 110, which is the first image.

Figure 13:
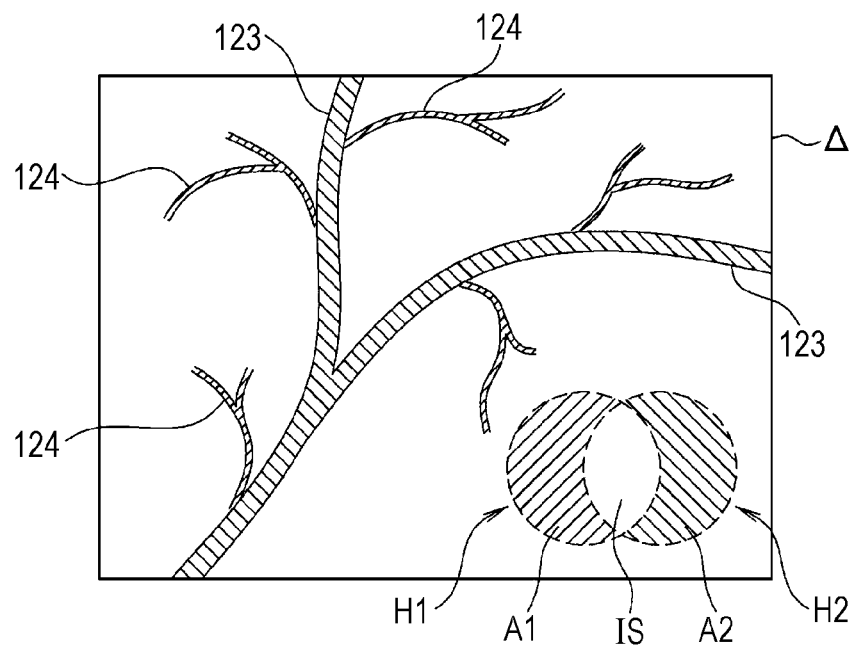
FIG. 13 is a schematic diagram of the difference image.
Figure 14:
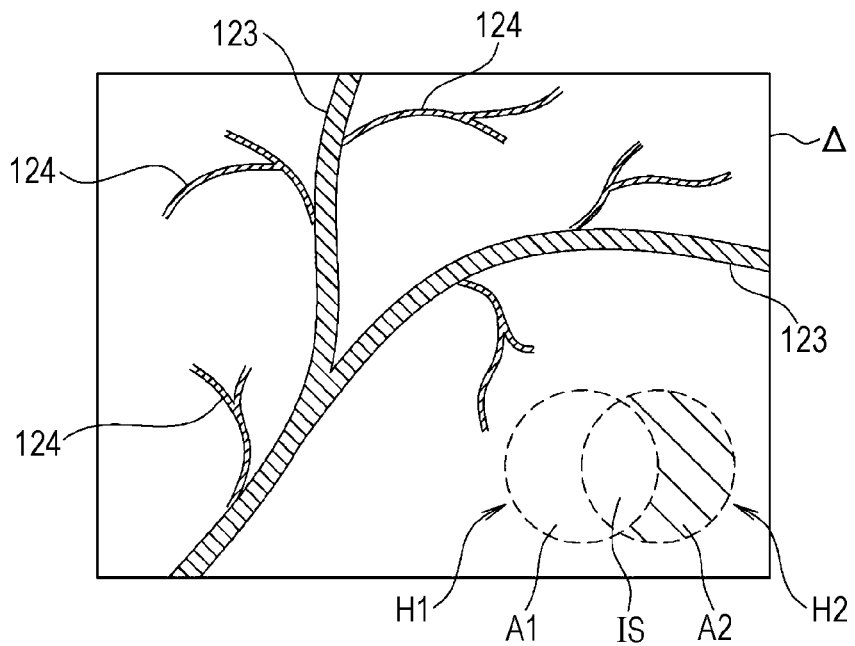
FIG. 14 is a schematic diagram of the difference image subjected to a saturation suppressing process.

Upon the halation-region detecting unit 74 detecting the halation region H1, the tone changing unit 75 performs the first saturation suppressing process and the second saturation suppressing process on the difference image Δ (S18). Specifically, the tone changing unit 75 performs the first saturation suppressing process on the difference image Δ (FIG. 13) and replaces the pixel values of the halation region H1 detected by the halation-region detecting unit 74 with approximately zero pixel values. Thus, as illustrated in FIG. 14, the region A1 and the overlap region IS have approximately zero pixel values as in the mucous membrane or the like. In addition, the tone changing unit 75 performs the second saturation suppressing process on the difference image Δ (FIG. 13) and sets the pixel values larger than or equal to the threshold Th to ±Th. Thus, the region A2 has substantially the same pixel values as the superficial blood vessel 123 (or slightly larger pixel values than the superficial blood vessel 123).

Figure 15:
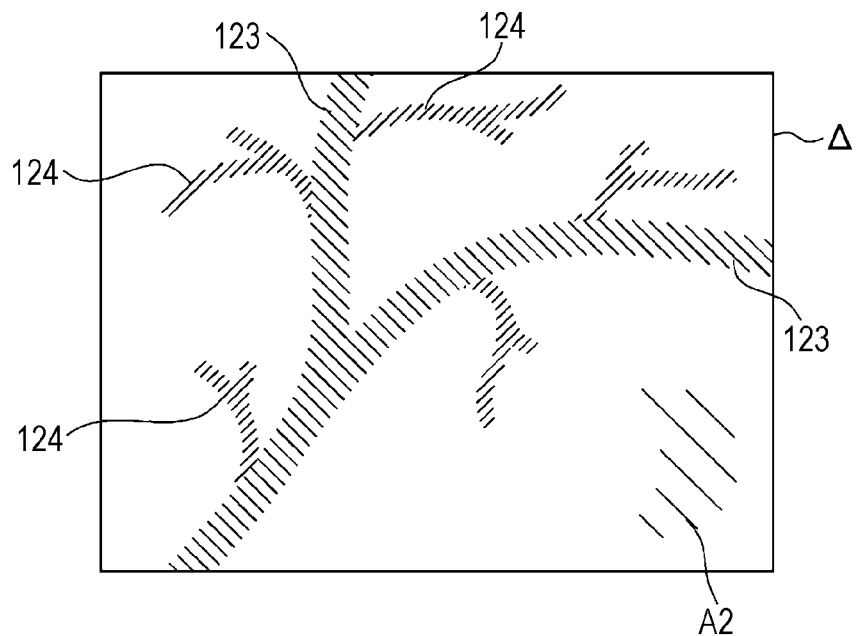
FIG. 15 is a schematic diagram of the difference image subjected to smoothing.

The difference image Δ (FIG. 14) subjected to the first saturation suppressing process and the second saturation suppressing process performed by the tone changing unit 75 is smoothed by the smoothing unit 76 (S19). As illustrated in FIG. 15, in the difference image Δ subjected to smoothing, boundaries between the most superficial blood vessel 124 or the superficial blood vessel 123 and the peripheral mucous membrane or the like are unclear and blur. The region A2 is in substantially the same state. In addition, although the region A1 and the overlap region IS have substantially the same pixel values as the mucous membrane or the like as a result of the first saturation suppressing process, differences from the mucous membrane or the like are further reduced as a result of smoothing. Thus, in the difference image Δ subjected to smoothing (FIG. 15), almost only the region A2 remains as the portion related to halation.

Figure 16:
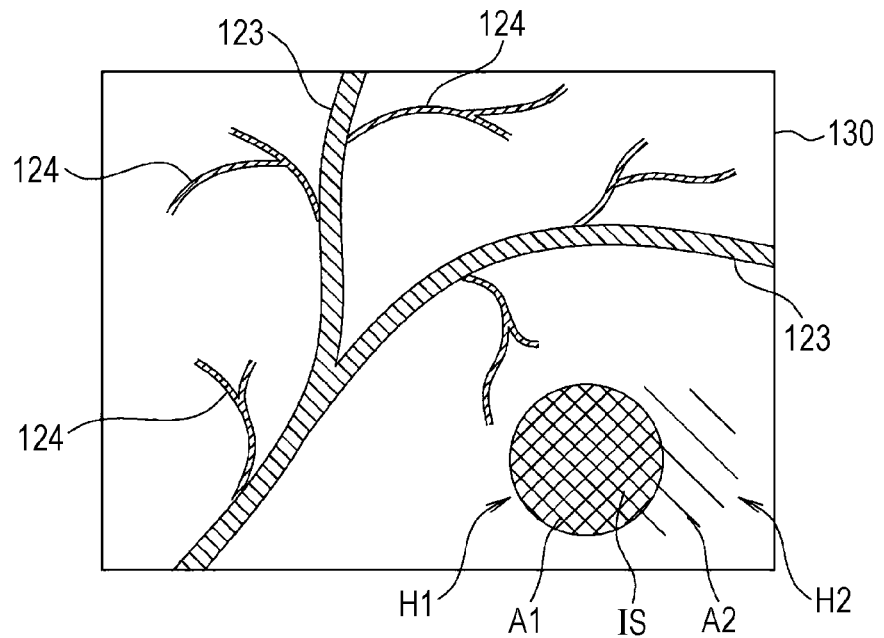
FIG. 16 is a schematic diagram of the difference image.

Upon the smoothing unit 76 smoothing the difference image Δ, the display-image generating unit 77 generates a display image 130 illustrated in FIG. 16 by using the first image or the second image and the difference image Δ subjected to smoothing (FIG. 15) (S20). In this embodiment, since the tissue of interest is the most superficial blood vessel 124, the display-image generating unit 77 generates the display image 130 by assigning the V image 110 to the luminance channel Y, the V image 110 having a higher contrast of the most superficial blood vessel 124 between the V image 110, which is the first image, and the B image 120, which is the second image. In addition, the display-image generating unit 77 assigns the difference image Δ subjected to smoothing (FIG. 15) to the chroma channels Cb and Cr by being multiplied by a weighting factor α and a weighting factor β, respectively. Accordingly, in the display image 130, in accordance with the pixel values of the difference image Δ, the most superficial blood vessel 124 is colored in a magenta-based color, and the superficial blood vessel 123 is colored in a cyan-based color. Thus, the display image 130 emphasizes the most superficial blood vessel 124 by using a color that is different from that of the superficial blood vessel 123, so that the most superficial blood vessel 124 is easily identified.

Since the region A1 and the overlap region IS have approximately zero pixel values in the corresponding portion in the difference image Δ, the portions related to the halation regions H1 and H2 are not colored and have a substantially achromatic color. Since the region A1 and the overlap region IS are the halation region H1 of the V image 110, which is the first image, the color is substantially white. On the other hand, since the difference image Δ has a suppressed pixel value −Th, the region A2 is colored in a magenta-based color as well as the superficial blood vessel 123 (or to have slightly stronger magenta color than the superficial blood vessel 123).

Figure 17:
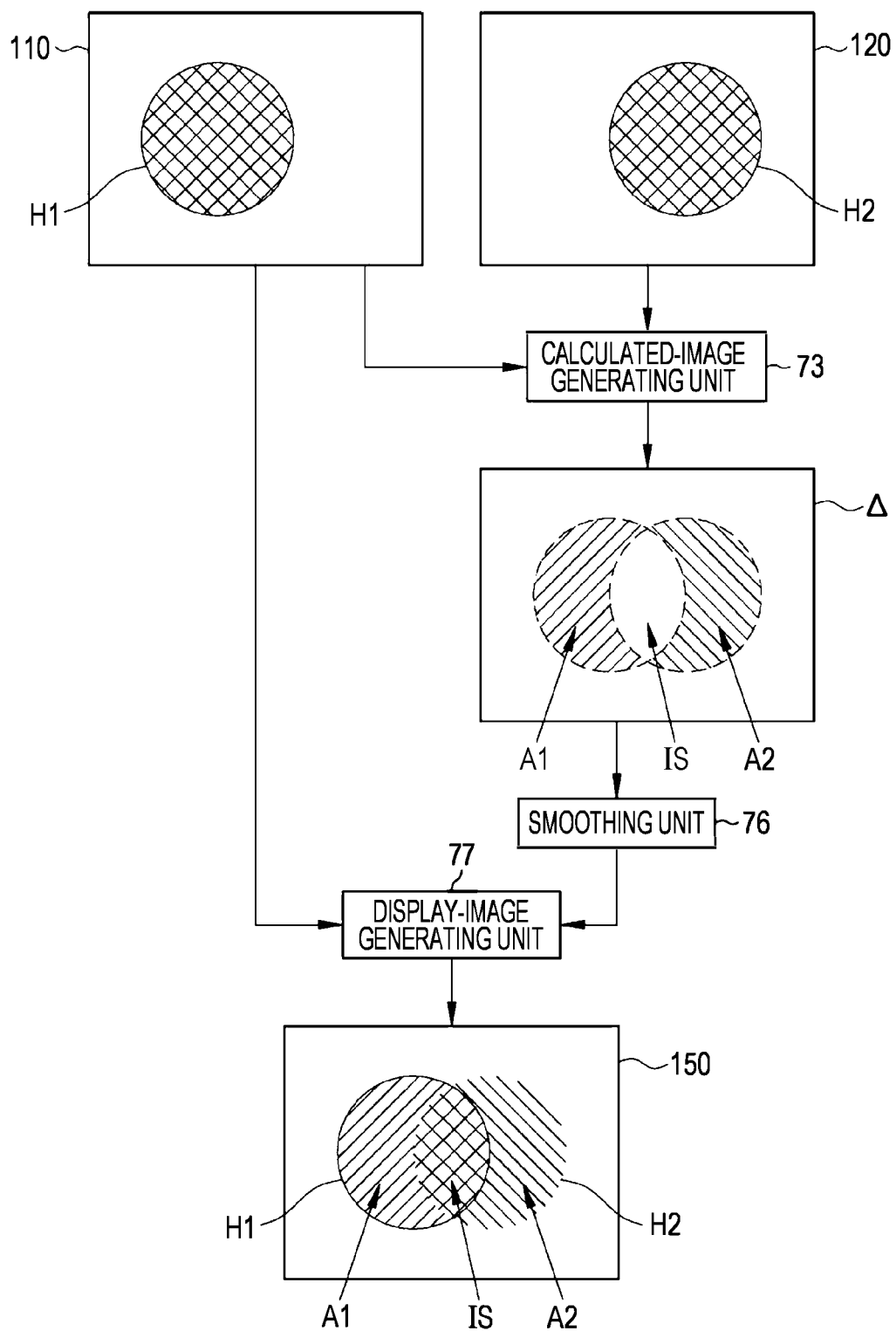
FIG. 17 is an explanatory diagram illustrating a display image of a comparative example and a generation process thereof.

Now, in order to compare the portions related to the halation regions H1 and H2, the following discusses a case in which a display image 150 is generated without the first saturation suppressing process and the second saturation suppressing process performed by the tone changing unit 75 on the difference image Δ. In this case, as only the portions related to the halation regions H1 and H2 are schematically illustrated in FIG. 17, substantially the same technique as the above-described endoscope system 10 is applied until a step in which the calculated-image generating unit 73 generates the difference image Δ, and the same difference image Δ as that illustrated in FIG. 13 is generated. However, the tone changing unit 75 does not perform processing on the difference image Δ, but the difference image Δ is smoothed to generate the display image 150. Thus, the portions related to the halation regions H1 and H2 in the display image 150 are colored in accordance with the pixel values of the region A1, the overlap region IS, and the region A2 of the difference image Δ before suppressing the saturation. Specifically, the region A1 is colored in a magenta-based color, the overlap region IS is colored in white, and the region A2 is colored in a cyan-based color. In addition, since the pixel values of the region A1 and the region A2 in the difference image Δ are not suppressed either, the region A1 is colored in an even stronger magenta-based color than the most superficial blood vessel 124, and the region A2 is colored in an even stronger cyan-based color than the superficial blood vessel 123. That is, the portions related to the halation regions H1 and H2 are colored in three colors. In addition, since the halation regions H1 and H2 are colored in the strongest colors compared with the other blood vessels and the like, and furthermore, the coloring is the same as that of the most superficial blood vessel 124 and the superficial blood vessel 123, the halation regions H1 and H2 are particularly outstanding in the display image 150.

In the display image 130 (FIG. 16) generated by the tone changing unit 75 performing the first saturation suppressing process and the second saturation suppressing process on the difference image Δ, the region A1 and the overlap region IS are white as bright as that of the original V image 110 (first image), and the region A2 is colored in a magenta-based color. Accordingly, the portions related to the halation regions H1 and H2 need only two colors for coloring. In particular, only one color, a magenta-based color, is a false color that is not present in the original V image 110 or the B image 120, and its range is restricted to the region A2, which is a portion of the halation regions H1 and H2. That is, the false color is reduced compared with a case in which the tone changing unit 75 does not perform the first saturation suppressing process and the second saturation suppressing process on the difference image Δ.

Furthermore, since the region A1 and the overlap region IS are white, it is easy to notice that the region A1 and the overlap region IS are the halation region H1. In addition, although the region A2 is colored in a magenta-based color, magenta is substantially the same color as that of the superficial blood vessel 123, and thus, the observation of the most superficial blood vessel 124 is unlikely to be hindered. In this light too, the false color is substantially reduced in the display image 130 (FIG. 16) generated by the tone changing unit 75 performing the first saturation suppressing process and the second saturation suppressing process on the difference image Δ, compared with a case in which the tone changing unit 75 does not perform the first saturation suppressing process and the second saturation suppressing process on the difference image Δ.

As described above, the endoscope system 10 and the processor device 16 generate the display image 130 in which the tone reflects a calculated image (difference image Δ) obtained by using a first image and a second image obtained by imaging an observation target by using different illumination light beams at different timings. At this time, since the tone changing unit 75 performs the first saturation suppressing process on the difference image Δ to suppress at least the saturation of the halation region H1 in the display image 130, thereby reducing a false color in the halation region H1. In addition, since the tone changing unit 75 performs the second saturation suppressing process on the difference image Δ to suppress the saturation of the region A2 too, and thereby a false color in the entire halation regions H1 and H2 can also be reduced.

Note that the halation region H2 in the B image 120 (second image) is not detected, the halation region H1 in the V image 110 (first image) is detected, and only the pixel values of the halation region H1 in the difference image Δ is replaced with zero in the above-described embodiment for the following reasons.

Figure 18:
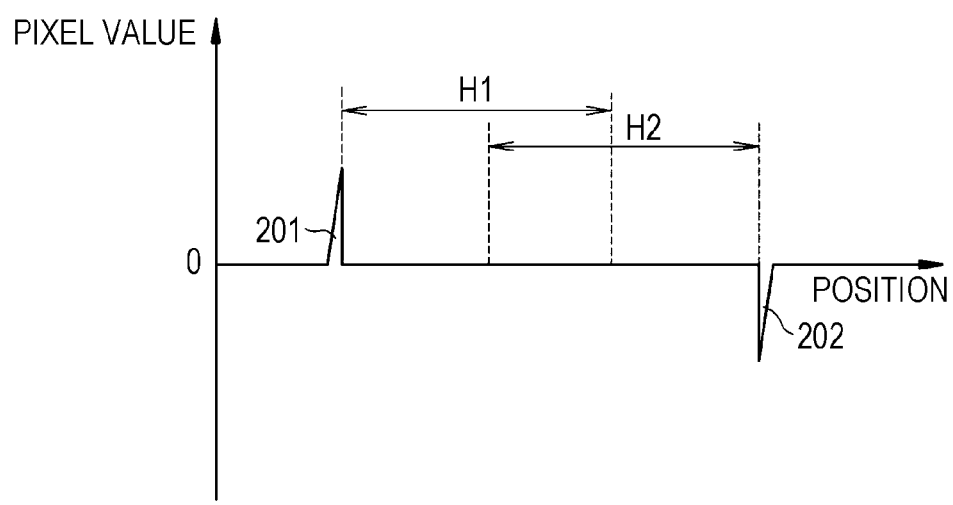
FIG. 18 is a graph illustrating a distribution of pixel values of the difference image in a case in which pixel values of halation regions in a first image and a second image are made zero.

First, as is clear from the detection method, the halation-region detecting unit 74 detects a set of pixels having larger than or equal to a fixed value (pixel value $P_B$) as the halation region. Accordingly, even when the first saturation suppressing process in which the pixel values of the halation region H1 in the difference image Δ (FIG. 7) are made approximately zero is performed, more strictly speaking, an end portion 201 of the halation region H1 remains as illustrated in FIG. 18. Similarly, even when the halation region H2 is detected and the pixel values of the halation region H2 in the difference image Δ (FIG. 7) are made approximately zero, an end portion 202 of the halation region H2 remains. Since these end portions 201 and 202 have substantially the same pixel values as the most superficial blood vessel 124 and the superficial blood vessel 123, depending on the thickness and the like, the end portions 201 and 202 are not removed in some cases even when smoothing by the smoothing unit 76 is performed.

Figure 19:
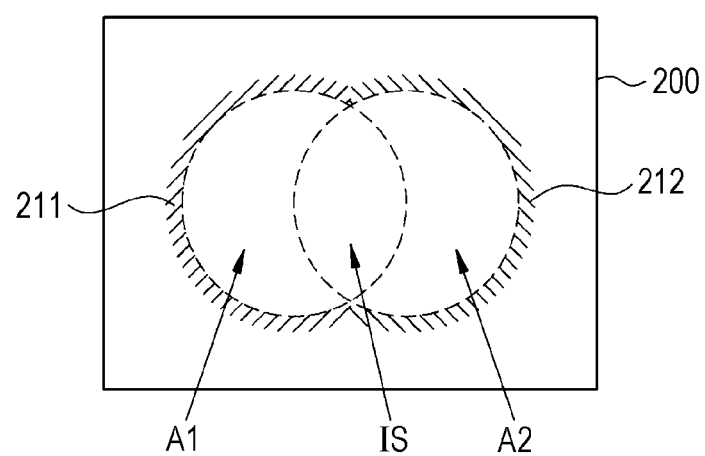
FIG. 19 is a schematic diagram of the difference image in a case in which the pixel values of the halation regions in the first image and the second image are made zero.
Figure 20:
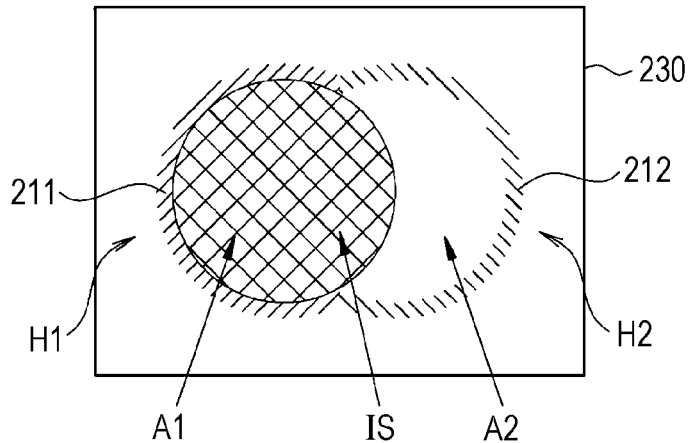
FIG. 20 is a schematic diagram of the difference image in a case in which the pixel values of the halation regions in the first image and the second image are made zero.

For example, it is assumed that both the halation region H1 and the halation region H2 are detected and that all the pixel values of the halation regions H1 and H2 in the difference image Δ (FIG. 13) are made approximately zero. In this case, as in a difference image 200 illustrated in FIG. 19, even if the pixel values of the region A1, the overlap region IS, and the region A2 are made approximately zero, outlines that are substantially the same as the most superficial blood vessel 124 and the superficial blood vessel 123 remain on a periphery 211 of the region A1 and a periphery 212 of the region A2. Accordingly, as illustrated in FIG. 20, in a display image 230 generated by using the above difference image 200, it is acceptable that the region A2 is not colored in a magenta-based color unlike in the display image 130 (FIG. 16) in the above-described embodiment. However, the periphery 212 of the region A2 is colored, and the region A2 is outlined in a magenta-based color. Thus, the display image 230 is extremely unnatural. Furthermore, since the magenta-based color of the periphery 212 of the region A2 is substantially the same as the magenta-based color of the superficial blood vessel 123, it may be erroneously recognized that the superficial blood vessel 123 is present.

Figure 21:
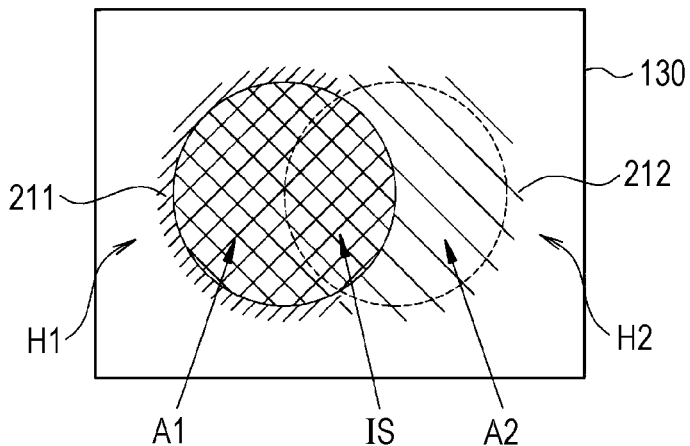
FIG. 21 is an enlargement diagram of a periphery of the halation regions in the display image.

On the other hand, in the display image 130 generated in the above-described embodiment, as illustrated in FIG. 21, even taking into account coloring of the peripheries 211 and 212 of the regions A1 and A2, the coloring features of the halation regions H1 and H2 are as described above and are substantially the same. Accordingly, in the endoscope system 10 and the processor device 16, the halation region H1 is detected only from the V image 110 (first image) that is assigned to the luminance channel Y of the display image 130, and only the halation region H1 is the target of the first saturation suppressing process. Thus, the endoscope system 10 and the processor device 16 prevents the halation regions H1 and H2 from becoming unnatural as a result of saturation suppressing for reducing a false color.

Note that although the halation-region detecting unit 74 detects the halation region H1 or H2 from the first image or the second image in the above-described embodiment, the halation-region detecting unit 74 can detect a portion related to the halation region H1 or H2 from the calculated image such as the difference image Δ. For example, by directly detecting a portion where the pixel values are extremely large (region A1) in the difference image Δ or a portion where the pixel values are extremely small (region A2) in the difference image Δ, the halation region H1 can be detected. The halation region H2 can be detected in a similar manner.

Although the tone changing unit 75 suppresses the saturation of the display image 130 for the halation regions H1 and H2 in the above-described embodiment, instead of changing the saturation of the display image 130, the tone changing unit 75 can change the hue or the brightness. In addition, it is also possible to change two or more of the saturation, the hue, and the brightness. In the case of the above-described embodiment, the hue can be changed by adjusting, for example, the values of the factors α and β. In addition, in the above-described embodiment, the brightness can be changed by correcting, for example, the pixel values of the first image assigned to the luminance channel Y.

Since only the halation region H1 of the first image (V image 110) is detected in the above-described embodiment, the tone of the halation region H1 in the first image (V image 110) is changed through the first saturation suppressing process, and the tone of the halation region H2 in the second image (B image 120) is changed through the second saturation suppressing process. However, it is possible to detect the halation region H2 in the second image and to change the tone of the halation region H2 in the second image through the first saturation suppressing process and to change the tone of the halation region H1 in the first image through the second saturation suppressing process. In addition, it is also possible to detect both the halation region H1 in the first image and the halation region H2 in the second image and to change the tone of both the halation regions H1 and H2 through the first saturation suppressing process. This is applicable to a case in which, even when the peripheries 211 and 212 of the halation regions H1 and H2 are outlined by a false color, the observation is not influenced in the relationship with the size of the tissue of interest or the like. In any case, the tone changing unit 75 can change the tone of both the halation regions H1 and H2 in the first and second images.

The calculated-image generating unit 73 generates the difference image Δ between the first image and the second image as the calculated image in the above-described embodiment. Instead, the calculated-image generating unit 73 may calculate the ratio between the first image and the second image. The ratio can be subjected to logarithmic transformation to be converted into the difference. Accordingly, the calculation of the ratio between the first image and the second image is substantially the same as the calculation of the difference image Δ in the above-described embodiment. In addition, since the most superficial blood vessel 124 is emphasized, the calculated-image generating unit 73 generates the difference image Δ between the first image and the second image as described above in the above embodiment. However, in a case of a different tissue of interest or the like, the calculated-image generating unit 73 can perform a calculation process other than the difference or ratio calculation (including a process using a function or a look-up table) in accordance with the tissue of interest or the like.

The display image 130 in which the tissue of interest (the most superficial blood vessel 124) is emphasized is generated and displayed in the above-described embodiment. However, the present invention is also suitably applied to, in addition to a case in which the tissue of interest or the like is emphasized, a case in which the tissue of interest or the like is extracted and a case in which biological function information (e.g., oxygen saturation) regarding the tissue of interest or the like is calculated. That is, the present invention is suitably applied to all the cases in which the tone of the display image reflects the difference between the first image and the second image obtained by imaging the observation target at different timings regardless of the type of processing that is to be performed last, such as emphasis, extraction, or calculation. In those cases, the calculated-image generating unit 73 generates a calculated image necessary for calculation of the biological function information.

In addition, the present invention is also suitably applied to a case in which the observation target is likely to move and in which the halation region H1 and the halation region H2 are likely to be misaligned. For example, the present invention is suitably applied to a case in which the observation target is enlarged to be observed or a case in which a mucous membrane or the like of a gullet, which is likely to be influenced by pulsation, is observed.

Figure 22:
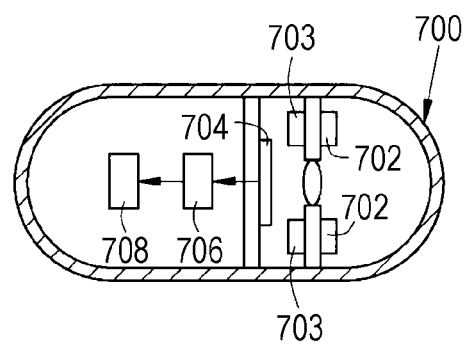
FIG. 22 is a schematic diagram of a capsule endoscope.

Although the present invention is implemented in the endoscope system that enables observation by inserting the endoscope 12 provided with the image sensor 48 into a subject in the above embodiment, the present invention is also suitably used for a capsule endoscope system. As illustrated in FIG. 22, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 serves in substantially the same manner as the light source control unit 22 and the control unit 52. In addition, the control unit 703 can wirelessly communicate with the processor device of the capsule endoscope system by using the transmission/reception antenna 708. The processor device of the capsule endoscope system is substantially the same as the processor device 16 according to the above embodiment, but the image processing unit 706 corresponding to the image acquiring unit 54 and the image processing unit 61 is provided in the capsule endoscope 700, and the display image 130 and the like that have been generated are transmitted to the processor device through the transmission/reception antenna 708. The image sensor 704 is configured in substantially the same manner as the image sensor 48.

REFERENCE SIGNS LIST

10 endoscope system
12 endoscope
12*a* insertion part
12*b* operating unit 12c bending part
12d tip part
12e angle knob
13a switch
13b zoom operating unit
14 light source device
16 processor device
18 monitor
19 console
20, 702 light source unit
20a V light source
20b B light source
20c G light source
20d R light source
22 light source control unit
30a illumination optical system
30b imaging optical system
41 light guide
45 illumination lens
46 objective lens
47 zoom lens
48, 704 image sensor
52, 703 control unit
54, 706 image acquiring unit
56 DSP
58 noise reducing unit
59 conversion unit
61 image processing unit
62 normal processing unit
63 special processing unit
66 display control unit
71 alignment unit
72 brightness correcting unit
73 calculated-image generating unit
74 halation-region detecting unit
75 tone changing unit
76 smoothing unit
77 display-image generating unit
110 V image
120 B image
123 superficial blood vessel
124 most superficial blood vessel
130, 150, 230 display image
200 difference image
201, 202 end portion
211, 212 periphery
700 capsule endoscope
708 transmission/reception antenna
A1, A2 region
Ad, As depth rang
H1, H2 halation region
IS overlap region
R0 range

What is claimed is:

1. An endoscope system comprising a processor configured to: acquire first image and a second image, the first image being obtained by imaging an observation target by using first illumination light, the second image being obtained by imaging the observation target by using second illumination light that is different from the first illumination light at a different timing from the first image; detect a halation region from at least one of the first image or the second image; perform calculation by using the first image and the second image and that generates a calculated image; generate a display image in which a tone reflects the calculated image; and change the tone of the halation region in the display image, wherein, when generating the display image, the processor is further configured to add a weight to the calculated image and assign the calculated image to a chroma channel, and wherein the processor is further configured to adjust the threshold by using the weight of the calculated image.

2. The endoscope system according to claim 1, wherein the processor is further configured to correct at least a pixel value of the calculated image to change the tone of the display image.

3. The endoscope system according to claim 2, wherein the processor is further configured to change at least one of a saturation, a hue, or a brightness.

4. The endoscope system according to claim 3, wherein the processor is further configured to suppress the saturation of the halation region in the display image.

5. The endoscope system according to claim 4, wherein the processor is further configured to make the halation region in the display image have an achromatic color.

6. The endoscope system according to claim 4, wherein the processor is further configured to suppress a degree of the pixel value of the calculated image to a threshold.

7. The endoscope system according to claim 1, wherein the processor is further configured to change at least one of a saturation, a hue, or a brightness.

8. The endoscope system according to claim 7, wherein the processor is further configured to suppress the saturation of the halation region in the display image.

9. The endoscope system according to claim 8, wherein the processor is further configured to make the halation region in the display image have an achromatic color.

10. The endoscope system according to claim 8, wherein the processor is further configured to suppress a degree of the pixel value of the calculated image to a threshold.

11. The endoscope system according to claim 1, wherein the processor is further configured to:
assign any one of the first image and the second image to a luminance channel and assigns the calculated image to the chroma channel to generate the display image,
detect the halation region from the one of the first image and the second image assigned to the luminance channel, and
change at least a tone of the halation region in the display image, the halation region being detected from the one of the first image and the second image assigned to the luminance channel.

12. The endoscope system according to claim 1, wherein the processor is further configured to change the tone of the halation region in the first image and the tone of the halation region in the second image.

13. The endoscope system according to claim 1, wherein the processor is further configured to generate, as the calculated image, a difference image between the first image and the second image.

14. The endoscope system according to claim 1, wherein the processor is further configured to detect the halation region by using a histogram representing an appearance frequency of the pixel value.

15. The endoscope system according to claim 14, wherein the processor is further configured to detect the halation region in a specific pixel-value range in a direction from a maximum pixel value to a smaller pixel value.

16. The endoscope system according to claim 15, wherein the processor is further configured to detect a peak of a valley of the histogram in the specific pixel-value range and detects, as the halation region, a set of pixels having pixel values larger than or equal to a pixel value at the peak of the valley and smaller than or equal to the maximum pixel value.

17. The endoscope system according to claim 1, wherein the processor is further configured to:
smooth the calculated image to be used by the display-image generating unit to generate the display image.

18. A method for operating an endoscope system according to claim 1, the method comprising: acquiring a first image and a second image, the first image being obtained by imaging an observation target by using first illumination light, the second image being obtained by imaging the observation target by using second illumination light that is different from the first illumination light at a different timing from the first image; detecting a halation region from at least one of the first image or the second image; calculating by using the first image and the second image to generate a calculated image; generating a display image in which a tone reflects the calculated image; and changing the tone of the halation region in the display image, wherein changing the tone of the halation region in the display image comprising changing the tone of the halation region in the first image and the tone of the halation region in the second image.

* * * * *